United States Patent [19]
Huber

[11] 4,080,833
[45] Mar. 28, 1978

[54] DEVICE FOR AUTOMATICALLY SUPPLYING LIQUID SAMPLES TO ANALYTICAL INSTRUMENTS

[75] Inventor: Bernard Huber, Uberlinger, Germany

[73] Assignee: Bodenseewerk Perkin-Elmer & Co., GmbH, Uberlingen, Germany

[21] Appl. No.: 772,216

[22] Filed: Feb. 25, 1977

[51] Int. Cl.² .............................................. G01N 1/12
[52] U.S. Cl. ..................................... 73/423 A; 23/259
[58] Field of Search ........................ 73/423 A; 23/259

[56] References Cited
U.S. PATENT DOCUMENTS

| 3,546,946 | 12/1970 | Smith | 73/423 A |
| 3,581,574 | 6/1971 | Smith | 73/423 A |

*Primary Examiner*—S. Clement Swisher
*Attorney, Agent, or Firm*—S. A. Giarratana; F. L. Masselle; E. T. Grimes

[57] ABSTRACT

A device for automatically supplying liquid samples to analytical instuments having a support member; a sample source mounted on the support member; a calibration vessel holder mounted on the support member for carrying a plurality of vessels containing neutral or calibration solutions, said holder being movable in a stepwise manner; an intake tube mounted for vertical reciprocating motion corresponding to predetermined points of an operating cycle; and wherein the support member is movable to a first position wherein the sample source is disposed adjacent the intake tube and to a second position wherein one of the vessels in the vessel holder is disposed adjacent the intake tube.

10 Claims, 7 Drawing Figures

DEVICE FOR AUTOMATICALLY SUPPLYING LIQUID SAMPLES TO ANALYTICAL INSTRUMENTS

BACKGROUND OF INVENTION

1. Field of Invention

This invention relates to devices for automatically supplying liquid samples to analytical instruments and, more particularly, to such devices wherein an intake tube is lowered into a sample source and at particular points in an operating cycle the intake tube is lowered into vessles containing neutal or calibration solutions.

2. Description of the Prior Art

In conventional prior art apparatus, the samples were contained in sample vessels, which were mounted in a circular array on a turntable, that was movable in a stepwise manner. During the movement of the turntable, the sample vessels one after the other would come into the area of a stationary intake tube, which was lowered therein to withdraw a liquid sample, that was thence supplied to the analytical instrument in an appropriate manner. It will be appreciated, that for quantitative analysis, it is necessary to calibrate the analytical instrument. For this purpose, a neutral solution, i.e. a solution that does not contain the substance being tested for, is supplied to the analytical instrument, in order to determine the zero line. In addition, a calibration solution, having a known concentration, is supplied to the analytical instrument and, by setting the signal evaluation circuit, the analytical instrument can then be adjusted so that an indication of zero is obtained with the neutral solution and an indication of the known value of the calibration solution is obtained with the calibration solution. It can then be assumed that the concentration of an unknown sample will be indicated correctly. However, in many analytical instruments, the calibration is dependent on the test condition, which may vary in the course of a series of measurements. Therefore, it is necessary to make another calibration after a certain number of analyses. For this purpose, prior art devices had vessels containing a neutral or null solution and vessels containing a calibration solution arranged in predetermined places in the circular array of sample vessels on the turntable. When these vessels came into the area of the intake tube, the analytical instrument would automatically be switched to its calibration mode. See, for example, German patent No. 2,111,609.

In prior art devices of the type described above, the vessels containing the neutral or calibration solutions were placed on the sample vessel turntable and the switching-over of the analytical instrument to its calibration mode was effected by the movement of the turntable, As a result, the capacity of the turntable was substantially reduced, because spaces which could otherwise be used for sample solutions were used by the neutral and calibration vessels. Moreover, the prior art devices were not flexible, as the calibration vessels could only be located in particular predetermined places on the turntable. Thus, it was impossible to vary the number of sample analyses between calibrations, depending on the respective requirements. In addition, it was difficult with prior art devices to use a plurality of different calibration solutions in the case of non-linear sensitivity characteristics. Moreover, such prior art devices involved the risk of faulty operation due to misplacement of the calibration vessels on the turbtable. It is further noted that in such prior art devices the samples, of necessity, had to be contained in vessels on a turntable.

SUMMARY OF THE INVENTION

The basic and general object of the present invention is the provision of a device for automatically supplying liquid samples to an analytical instrument, which is an improvement over such prior art devices, as will become apparent as the description proceeds.

Other objects of the invention reside in the provision of a device for automatically supplying liquid samples to analytical instruments; with which the number of analyses between calibrations can be varied as desired or necessary; with which, if a turntable is used for feeding the samples, the capacity of the turntable can be fully utilized for the accomodation of samples; which does not necessarily require the use of a turntable as a sample source but enables the use of other types such as, for example, an overflow vessel through which the liquid to be examined continuously flows; with which a plurality of different calibration solutions may be used, if desired or required; and which reduces the risk of faulty operation.

To the accomplishment of the foregoing objectives, and additional objects and advantages which will become apparent as this description proceeds, the invention contemplates the provision of a new and improved device for automatically supplying liquid samples to an analytical instrument wherein the vessels containing the neutral or calibration solutions are mounted in a separate calibration vessel holder that is movable in a stepwise manner, and the sample source and the calibration vessel holder are both mounted on the same support, which is movable between two positions. In the first position of the support, the sample source is positioned in the area of the intake tube and in the second position thereof, the calibration vessel holder is positioned in the area of the intake tube. As a result, the timing of the calibration procedure is not determined by the placement of the calibration vessels on the sample vessel turntable, but by the movement of the support, which movement can be initiated at any desired time. It will be appreciated, that with the device of the present invention, it is not necessary for the sample source to be in the form of a turntable, as other suitable sample sources may be arranged on the support. The calibration vessel holder may contain any desired number of calibration vessels, thereby to determine non-linear calibration characteristics.

In one form of the invention, the sample source comprises a sample vessel holder, a plurality of sample vessels carried by this holder, and means for moving the sample vessel holder in a stepwise manner so that one of said sample vessels is positioned adjacent the intake tube when the support is in its first position. According to one aspect of the invention, the sample vessel holder comprises a turntable having a circular array of sample vessels therein, and the calibration vessel holder comprises a second turntable having a circular array of vessels therein, and the support member is a base plate mounted for pivotal movement about a pivot axis for movement between two stop members to determined said first and second positions, the pivot axis being located outside the plane of the axes of rotation of the two turntables and parallel thereto.

According to another aspect of the invention, the turntables are in driving connection with ratchet wheels respectively, and means are provided for vertically reciprocating the intake tube, which include a motor that simultaneously reciprocates a slide bar extending intermediate the turntables. The slide bar carries two pawls, one of which engages the ratchet wheel of the sample vessel turntable when the base plate is in its first position and the other pawl engages the ratchet wheel of the calibration vessel when the base plate is in its second position. In this way a single motor is able to both control the movement of the intake pipe as well as effecting the correct stepping of both turntables.

According to one feature of the invention, the calibration procedure is initiated and terminated by control elements that are removably attachable to the sample vessel turntable, said control elements being positioned to release the base plate for rotary movement from its first position to its second position at a predetermined angular position of the sample vessel turntable. A control element is attached to the calibration vessel turntable that is positioned to release the base plate for rotary movement from its second position to its first position at a predetermined angular position of the calibration vessel turntable. Thus, each control element on the sample vessel turntable initiates a calibration procedure, which continues to the end thereof, and then the return of the base plate is effected by the control element on the calibration vessel holder.

According to another feature of the invention, the same motor is also used to rotate the base plate. This is effected by the provision of a projection projecting from the slide bar in a direction parallel to the pivot axis of the base plate. A pawl having two inclined surfaces arranged in a roof-like manner is pivotally mounted on the base plate in the path of this projection. The tip of the pawl is rotated by resilient means with respect to the projection in a direction towards the second position when the base plate is in its first position, and in a direction towards the first position when the base plate is in its second position. Controlled stop members are mounted, respectively, to limit the rotary movement of the pawl in both directions, said stop members being controlled by the control elements attached to the turntables, respectively. In operation, the projection from the slide bar, during the forward movement thereof and when the base plate is in its first position, engages one inclined surface of the pawl to urge it towards the second position. When the stop has not been set, the pawl yields so that the base plate remains in its first position. When the rotary movement of the pawl is limited by the stop (set by the control element on the sample vessel turntable), the whole base plate is rotated to its second position by the action of the projection on the inclined surface. In this second position, the pawl is rotated towards the first position by a resilient element to thereby position the opposite inclined surface of the pawl in the path of the projection so that forward movement of the slide bar will result in returning the base plate to its first position, if, after completion of the calibration procedure the rotary movement of the pawl is limited by the stop set by the control element on the calibration vessel turntable.

There has been thus outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as a basis for the designing of other devices for carrying out the several purposes of the invention. It is important, therefore, that the claims be regarded as including such equivalent devices as do not depart from the spirit and scope of the invention.

Specific embodiments of the invention have been chosen for purposes of illustration and description, and are shown in the accompanying drawings, forming a part of the specification.

DETAILED DESCRIPTION OF A PREFERRED EMBODIMENT

Figure 1:
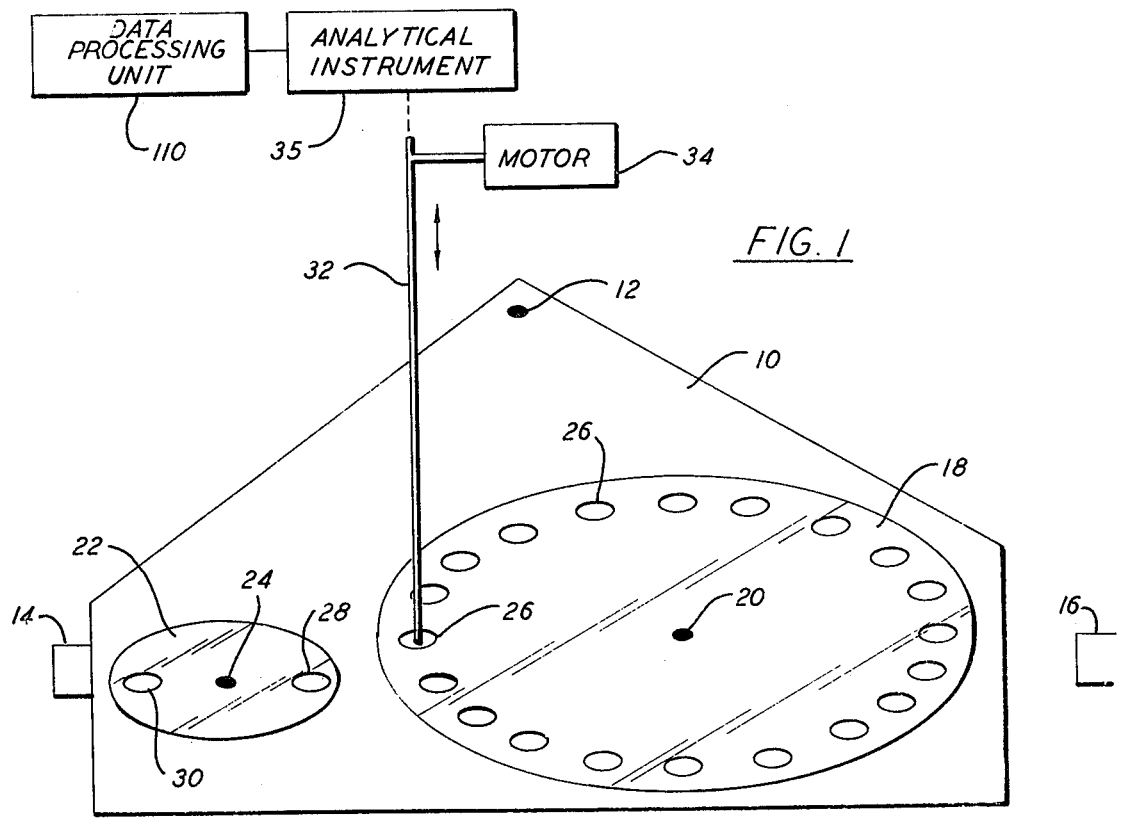
FIG. 1 is a schematic representation of a device for automatically supplying liquid samples to analytical instruments according to the invention.

As illustrated in FIG. 1, the device for automatically supplying liquid samples to analytical instruments comprises a base plate 10 mounted for pivotal movement about an axis 12 between two stop members 14 and 16. A sample vessel turntable 18 is mounted on the base plate 10 for rotation about an axis 20, and a calibration vessel turntable 22 is mounted on the same base plate for rotation about an axis 24.

The sample vessel turntable 18 carries a circular array of sample vessels 26, which accomodate the liquid samples to be tested, while the calibration vessel turntable 22 carries at least a pair of calibration vessels, one being provided to accomodate a neutal solution, i.e. a solution not containing the substances being tested for, and the other being provided to accomodate a calibration solution of known concentration. It is noted that the axis 12 of the base plate is located outside the plane defined by the axes 20 and 24. When the base plate 10 engages the stop member 14, it is in its first position, wherein a sample vessel 26 is located below an intake pipe or tube 32. This intake pipe is neither rotatable with the base plate nor rotatable with turntables, but is arranged for vertical reciprocating motion 34, so as to be lowered into the sample vessel 26. The sample liquid is taken in and fed through the intake pipe to an analytical instrument 35 such as, for example, an atomic absorption spectrometer. By stepwise advancement of the sample vessel turntable 18, the various sample vessels 26 are moved consecutively below the intake pipe 32.

Still referring to FIG. 1, if a calibration is to be made such as, for example, after each five analyses, the base plate 10 is rotated to its second position, wherein it engages the stop member 16. In this position the vessel 28 containing the neutral solution is located below the intake pipe 32. By means of a contact (not shown) the analytical instrument is switched to its calibration mode. Neutral solution is taken from the vessel, and the zero line of the analytical instrument is balanced on the basis of the signal obtained thereby. After the intake pipe has been lifted, the calibration vessel turntable is advanced, whereby the vessel 30 is moved under the intake pipe. The intake pipe is lowered into the vessel 30, and calibration solution is supplied to the analytical instrument 35. The analytical instrument is corrected in accordance therewith, if necessary, so that it corresponds to the known concentration of the calibration solution. After completing this calibration procedure, the base plate 10 is rotated back to its first position wherein the sample vessels 26 are again disposed under the intake pipe and the analysis procedure continues.

The operational steps of the device may be controlled electrically, with each movement being effected by means of individual servomotors. However, this would require, in addition to the servomotor 34, one servomotor for each turntable 18, 22 and one servomotor for rotating the base plate 10. FIGS. 2 to 6 show one form of the invention wherein all movements are derived from the single servomotor 34.

Figure 2:
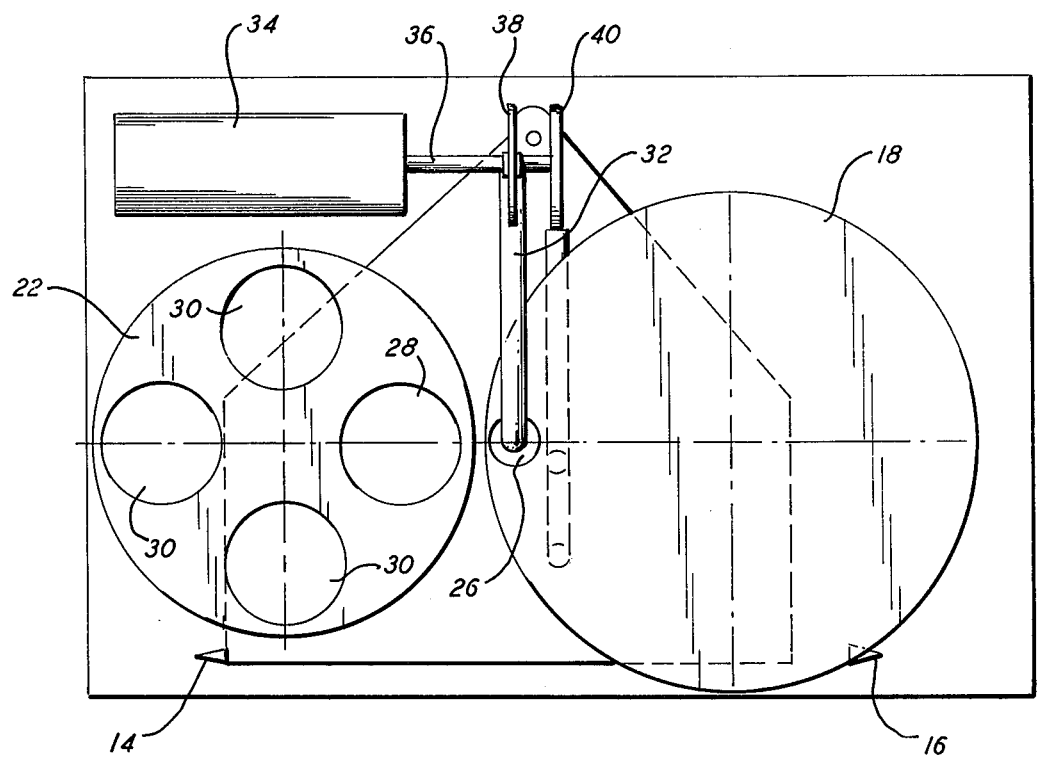
FIG. 2 is a plan view of an embodiment of a device constructed according to the concepts of the present invention.
Figure 4:
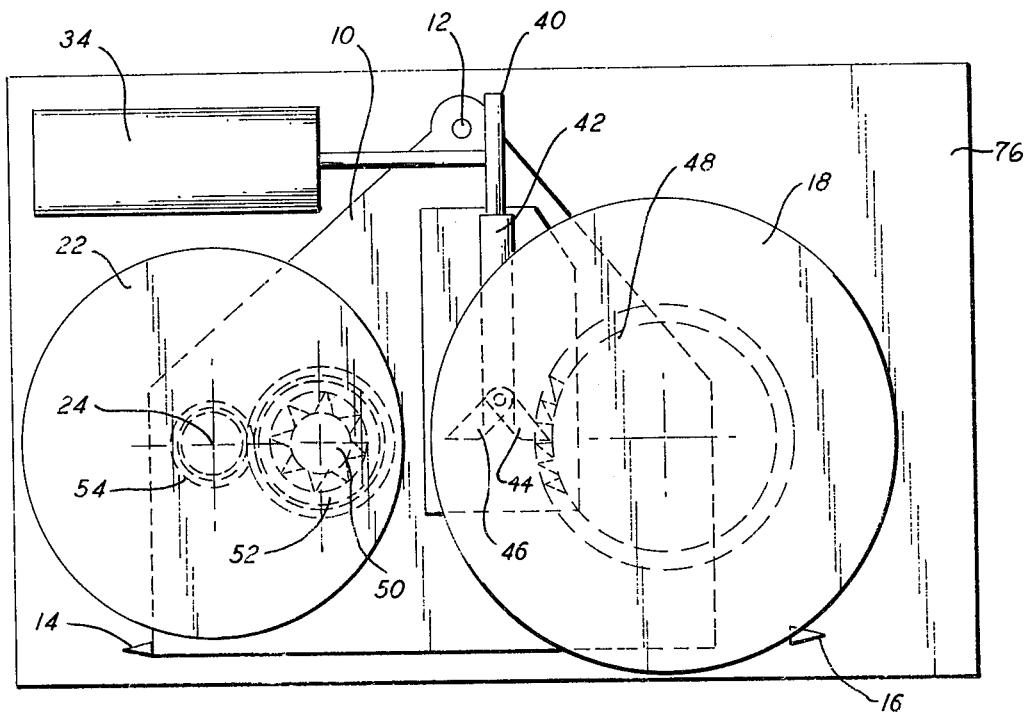
FIG. 4 is a plan view showing a mechanism for effecting stepwise movement of the turntable of the device.

As best seen in FIG. 2, cams 38 and 40 are mounted on the shaft 36 of the servomotor 34, with the cam 38 being arranged to lower the intake pipe 32 into the sample vessels 26 mounted on the turntable 18 and to lift it again. The cam 40 is arranged, as best seen in FIG. 4, to reciprocate a slide bar 42, which (in a manner not shown) is guided for rectilinear movement in a stationary guide and extends intermediate the two turntables 18 and 22. Two pawls, 44 and 46, are pivotally mounted and arranged at angles, respectively, on opposite sides of the slide bar 42. A ratchet wheel 48 is affixed to the sample vessel turntable 18. In the first position of the base plate 10, i.e. adjacent the stop member 14, the pawl 44 engages the ratchet wheel 48, thereby, with each revolution of the motor 34, and thus with each lowering and lifting movement of the intake pipe 32, and with each reciprocating movement of the slide bar 42, the sample vessel turntable 18 is advanced by one step so that the next adjacent sample vessel will be positioned under the intake pipe. The cams 38 and 40 are so oriented with respect to each other that the advancement of the turntable by the cam 40 is effected, when the intake pipe has been lifted out of the sample vessel 26 and by the cam 38.

Still referring to FIG. 4, in the second position, or when the base plate 10 engages the stop 16, the pawl 46 engages a ratchet wheel 50, which is coupled to the shaft 24 of the calibration vessel turntable through gears 52 and 54. In this position of the base plate, one of the calibration vessels 28, 30 of the calibration vessel turntable 22 is located below the intake tube 32, the turntable 22 is advanced through one step by each reciprocating movement of the slide bar 42, whereby the next calibration vessel is positioned under the intake pipe.

Figure 5:
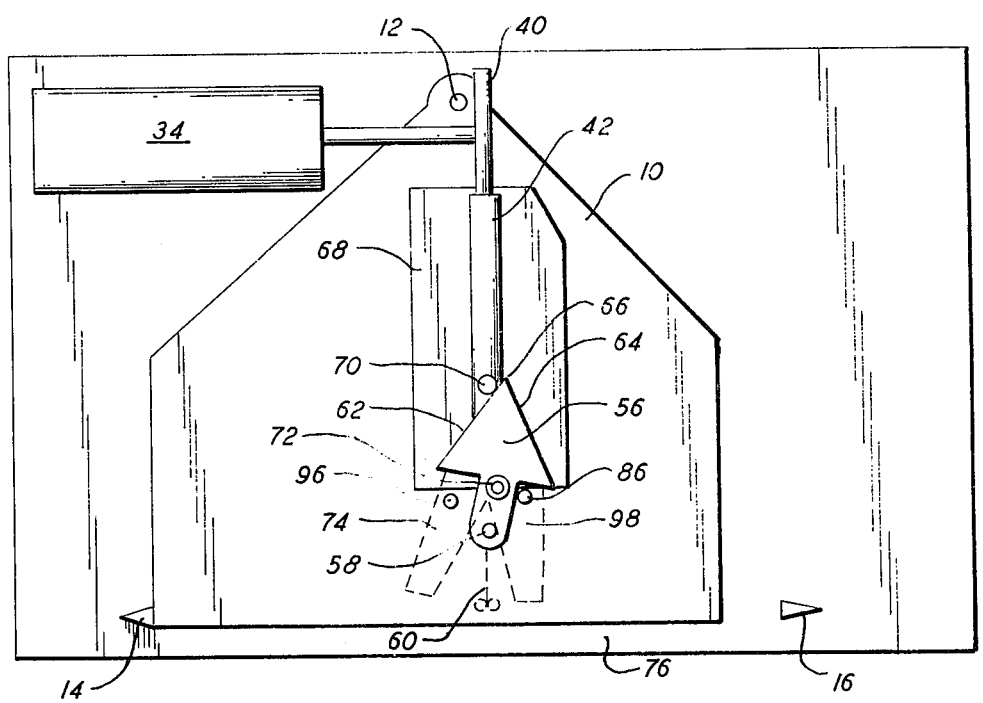
FIG. 5 is a plan view of a mechanism for initiating rotary movement of the base plate of the device.

A pawl 56, FIG. 5, is mounted on the base plate 10 for pivotal movement about an axis 58. This pawl is resiliently restrained towards a central position with respect to the base plate 10 by a leaf spring 60, provided for the purpose. The pawl 56 has two inclined surfaces 62 and 64 arranged in a roof-like manner to form a tip 66 therebetween. A projection 70 is provided on the slide bar 42 that extends upwardly through an aperture 68 in the base plate. The pawl 56 is located in the path of this projection. Furthermore, a projection 72 is provided on the pawl 56. When the base plate is in its first position, the projection 72 engages a leaf spring 74 which is mounted on a support plate 76. Due to the action of this leaf spring 74, the tip 66 of the pawl 56 is rotated in a direction towards said second position, whereby the inclined surface 62 is moved into the path of the projection 70. During a stroke of the slide bar 41, the pawl 56 is normally moved sidewardly. In this case the base plate 10 remains in its first position, and during the return stroke of the slide bar, the pawl 56 is returned to its position, as shown in FIG. 5, under the action of the spring 60.

Figure 6:
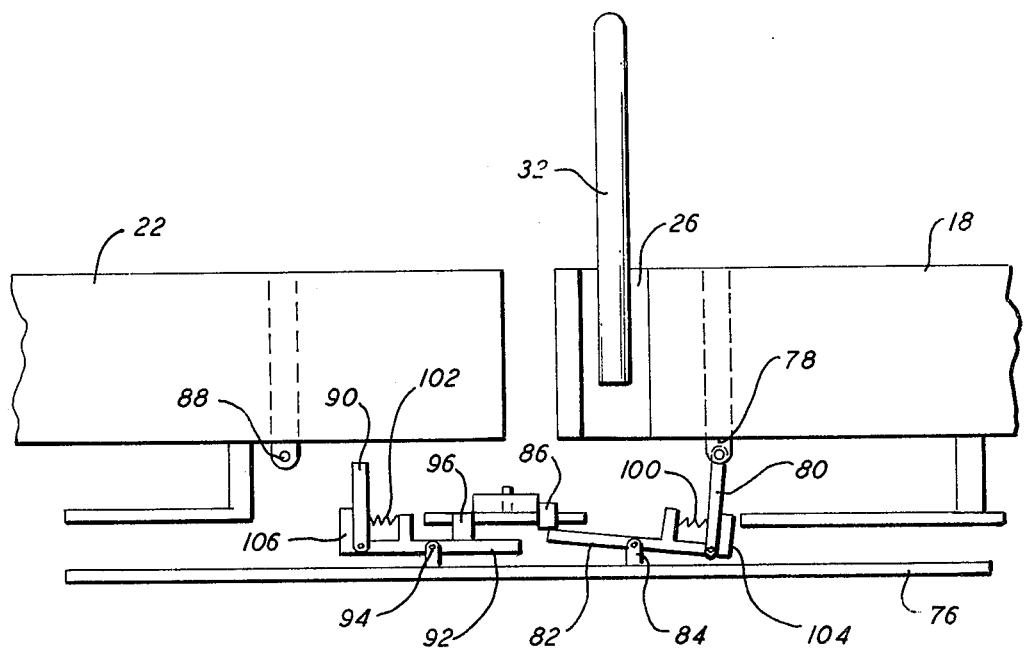
FIG. 6 is a side elevation of the mechanism of FIG. 5.

As best illustrated in FIG. 6, after a predetermined number of analyses, a two-armed lever 82 is tilted by a cam 78 removably attached to the sammple vessel turntable 18 through an intermediate element 80. The lever 82 is pivoted about a horizontal axis in a bearing support 84 on the support plate 76. A stop pin 86, which is slidably guided in the base plate 10, is displaced upwardly into its operative position by the inner end of the lever 82. During the next stroke of the slide bar 42, the pawl 56 engages the stop pin 86, FIG. 5, and cannot yield further. As a result, the whole base plate is rotated by the projection 70 acting on the inclined surface 62. Thus, the base plate is moved to its second position, wherein it engages the stop member 16, for purposes of calibration and advancement of the calibration vessel turntable 22.

As best seen in FIG. 6, a control cam 88 is removably affixed to the calibration vessel turntable 22. After completion of the calibration procedure, this cam engages a two-armed pivot lever 92 through an intermediate element 90, the lever being pivotable about a horizontal axis in a bearing support 94. The inner end of the pivot lever 92 is engageable with a stop pin 96, which is slidably guided in the base plate 10, to thereby move the pin into operative position.

In the second position of the base plate 10, the pin 72 engages a leaf spring 98, which is mounted on the support plate 76, to urge the pawl 56 in a counterclockwise direction, i.e. to rotate the tip 66 towards its first position. This action serves to position the inclined surface 64 in the path of the projection 70. When the stop pin, FIG. 6, is in its operative position, the pawl 56 cannot yield to the projection during the stroke of the slide bar 42, and hence the whole base plate is rotated back to its first position.

Still referring to FIG. 6, the intermediate elements 80 and 90 are pivotally connected to the pivot levers 82 and 92, respectively, for inward pivotal movement and to engage stops 104 and 106, under the action of springs 100 and 102, respectively, whereby they extend substantially normal to their respective pivot levers in their positions of rest. If the base plate is rotated, in the manner described, from its first position to its second position, the control cam 88 moves into the area of the pivot lever 92 but does not initially cause pivotal movement of the lever 92 because of the resilient yielding of the intermediate element 90. Only after a subsequent revolution of the calibration vessel turntable 22, when the control cam 88 moves the intermediate element in a peripheral direction rather than in a radial direction will there be a pivotable movement of the lever 92. A similar operative effect is obtained due to the intermediate element 80 during rotation of the base plate 10 back to its first position.

It will be appreciated that the control cams 78 and 88 are adapted to be removably mounted on the turntables in any desired locations at the option of the user and, as a result, it is possible to effect calibration as required, such as after every fifth or after every tenth analysis, for example. Moreover, each calibration cam comprise two or more steps, as required. FIG. 2, for example, shows a calibration vessel turntable 22 designed to accomodate four calibration vessels.

While mechanical means have been described for controlling the stop pins 86 and 96, it is also within the contemplation of this inventin to employ electromagnetic means for this purpose.

Figure 1A:
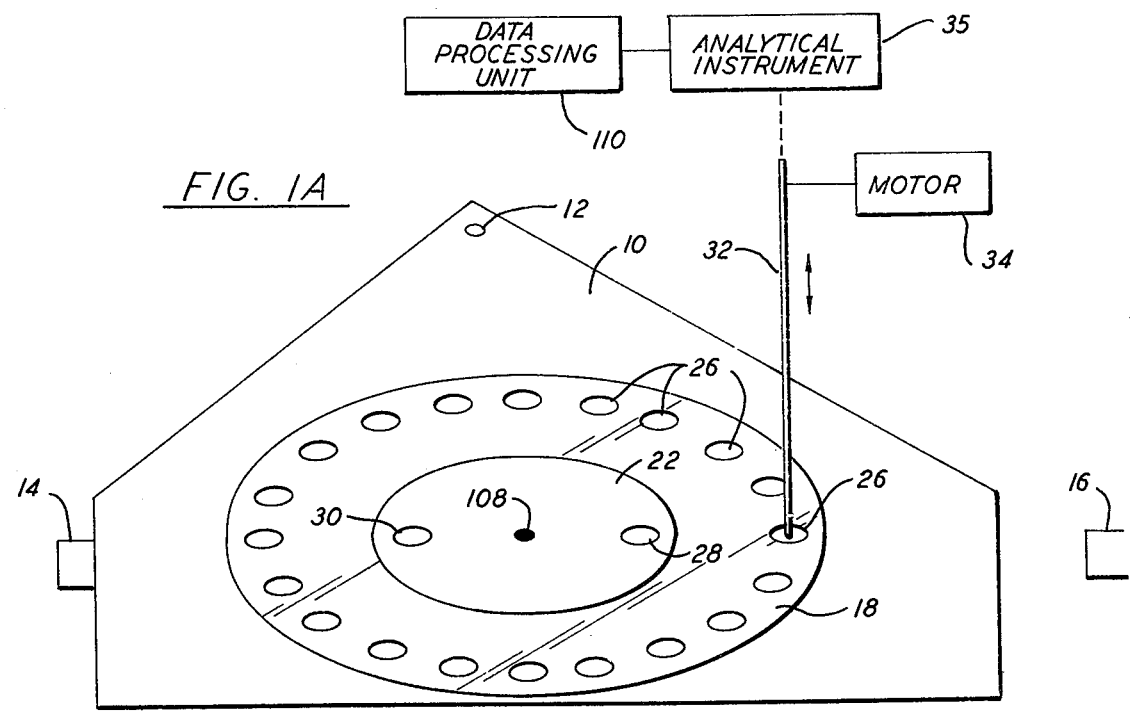
FIG. 1A is a schematic representation of a device similar to FIG. 1, but showing another embodiment of the invention.
Figure 3:
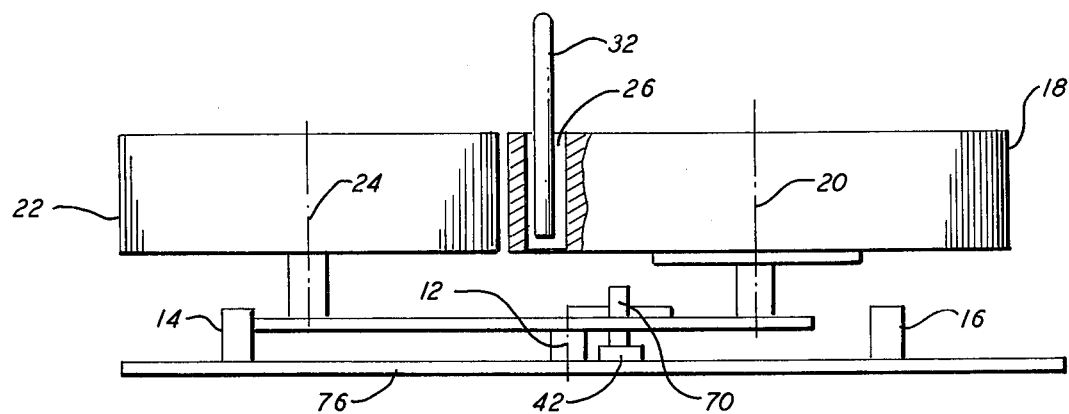
FIG. 3 is a side elevation of the device of FIG. 2.

The arrangement of the elements in the device of the invention may be modified in various ways, such as, for example, as shown in FIG. 1A, in order to save working area, the two turntables 20 and 22 may be concentrically arranged about an axis 108 with the table having the smaller diameter being placed inside the other table. The mode of operation and driving could be the same with the concentric arrangement of the vessels, as in the arrangement of FIGS. 2 to 6.

In installations where it is desirable to save analytical time, it is possible to effect the calibration, not in accordance with a rigid timing schedule, but only when required. In instruments having a data processing unit connected thereto, as indicated at 110 in FIG. 1, this can be achieved by making the number of samples investigated, between two consecutive calibration procedures or cycles under the control of the data processing unit 110, dependent on the drift between the first of said two calibration cycles and the next preceding calibration cycle. Thus, by extrapolation, from the drift results from each two consecutive calibrations, the data processing unit 110 automatically determines by means of a read-in program the number of samples to be taken before the next calibration procedure is initiated.

Thus, an improved device for automatically supplying liquid samples to an analytical instrument has been shown. Although specific embodiments have been illustrated and described, it will be obvious to those skilled in the art that various modifications may be made without departing from the spirit of the invention, which is to be limited solely by the appended claims.

What is claimed is:

1. A device for automatically supplying liquid samples to an analytical instrument comprising, in combination:
   a support member in the form of a base plate mounted for pivotal movement about a pivot axis;
   a sample source mounted on said support member;
   a calibration vessel holder mounted on said support member which comprises a turntable having a circular array of vessels containing neutral or calibration solutions, said calibration vessel holder being movable in a stepwise manner;
   an intake tube, means for vertically reciprocating said intake tube corresponding to predetermined points of an operating cycle; and
   means for pivoting said support member about said pivot axis to a first position wherein said sample source is disposed adjacent said intake tube and for pivoting said support member about said pivot axis to a second position wherein one of said vessels in said vessel holder is disposed adjacent said intake tube, said pivot axis being offset with respect to the axis of rotation of said turntable and parallel thereto.

2. A device according to claim 1 wherein said sample source is a turntable with a circular array of vessels, said sample vessel and said calibration vessel turntables being disposed in concentric relationship with respect to each other.

3. A device for automatically supplying liquid samples to an analytical instrument comprising, in combination:
   a base plate mounted for pivotal movement about a pivot axis for movement between two stop means to determine first and second positions;
   a sample vessel turntable having a circular array of sample vessels therein mounted on said base plate;
   a calibration vessel turntable having a circular array of vessels therein mounted on said base plate for containing neutral or calibration solutions;
   an intake tube, means for vertically reciprocating said intake tube corresponding to predetermined points of an operating cycle;
   means for moving said sample vessel turntable in a stepwise manner so that one of said sample vessels is positioned adjacent said intake tube when said base plate is in its first position;
   means for moving said calibration vessel turntable in a stepwise manner so that one of said calibration vessels is positioned adjacent said intake tube when said base plate is in its second position; and
   means for moving said base plate to said first position wherein one of said sample vessels is disposed adjacent said intake tube and for moving said base plate to said second position wherein one of said calibration vessels is adjacent said intake tube, said pivot axis being located outside the plane of the axes of rotation of said two turntables and parallel thereto.

4. A device according to claim 3 wherein said turntables are in driving connection with ratchet wheels respectively, and wherein said means for vertically reciprocating the intake tube includes a motor, said motor simultaneously reciprocating a slide bar extending intermediate the turntables, said slide bar carrying two pawls, one of said pawls engaging the ratchet wheel of the sample vessel turntable when the base plate is in its first position, and the other of said pawls engaging the ratchet wheel of the calibration vessel turntable when the base plate is in its second position.

5. A device according to claim 4 wherein control elements are attached to the sample vessel turntable, said control elements being positioned to release the base plate for rotary movement from ints first position to its second position at a predetermined angular position of the sample vessel turntable; and wherein a control element is attached to the calibration vessel turntable, said last named control element being positioned to release the base plate for rotary movement from its second position to its first position at a predetermined angular position of the calibration vessel turntable.

6. A device according to claim 5 wherein said slide bar has a projection projecting therefrom in a direction parallel to the pivot axis of the base plate, a pawl having two inclined surfaces arranged in a roof-like manner being pivotally mounted on the base plate in the path of said projection, the tip of said pawl being rotated by resilient means with respect to said projection in a direction towards the second position when said base plate is in its first position and in a direction towards the first position when the base plate is in its second position, and wherein controlled stop members are mounted respectively to limit the rotary movement of said pawl in both directions, said stop members being controlled by the control elements attached to the turntables, respectively.

7. A device according to claim 6 wherein said pawl is resiliently restrained, with respect to the base plate, to a central position of rest by a spring.

8. A device according to claim 7 wherein said stop members are stop pins guided for sliding movement in the base plate, and wherein said control elements attached to the turntables are cams, and wherein means including two-armed levers move said stop pins corresponding to movement of said cams, respectively.

9. A device according to claim 8 wherein said means for moving said stop pins include intermediate elements pivotally mounted for inward rotary movement on said two-armed levers respectively, and spring means for urging said intermediate elements outwardly in positions wherein the intermediate elements extend substantially normal to the levers in the direction toward said cams, respectively.

10. A device according to claim 9 wherein said cams are separable from said turntables respectively, said cams being attachable at a plurality of predetermined locations on the turntables, respectively.

* * * * *